US00PP15187P3

(12) United States Plant Patent
Cullina

(10) Patent No.: US PP15,187 P2
(45) Date of Patent: Sep. 28, 2004

(54) ***POLEMONIUM REPTANS* NAMED 'STAIRWAY TO HEAVEN'**

(50) Latin Name: *Polemonium reptans*
Varietal Denomination: Stairway to Heaven

(75) Inventor: William Cullina, Hopkinton, MA (US)

(73) Assignee: New England Wildflower Society, Framingham, MA (US)

( * ) Notice: Subject to any disclaimer, the term of this patent is extended or adjusted under 35 U.S.C. 154(b) by 0 days.

(21) Appl. No.: 10/213,866

(22) Filed: Aug. 7, 2002

(65) Prior Publication Data

US 2004/0031078 P1 Feb. 12, 2004

(51) Int. Cl.[7] ..... A01H 5/00

(52) U.S. Cl. ..... Plt./263

(58) Field of Search ..... Plt./263

(56) References Cited

U.S. PATENT DOCUMENTS

| | | | | |
|---|---|---|---|---|
| PP9,781 P | 1/1997 | Proteau et al. | ..... | Plt./263 |
| PP13,441 P2 | 12/2002 | Heims et al. | ..... | Plt./263 |

*Primary Examiner*—Kent Bell
(74) *Attorney, Agent, or Firm*—Beth E. Arnold; Foley Hoag LLP

(57) ABSTRACT

A new and distinct cultivar of *Polemonium* plant named Stairway to Heaven, characterized by its distinct white and gray variegated foliage with violet flowers beginning in May and continuing to flower for 14–21 days in mid-spring.

1 Drawing Sheet

Latin name: *Polemonium reptans.*
Variety denomination: 'Stairway to Heaven'.

BACKGROUND OF THE INVENTION

The present invention relates to a new distinctive cultivar of a hardy perennial herabaceous plant of the genus *Polemonium,* a member of the *Polemoniaceae* family, and the species *reptans,* known by the cultivar name 'Stairway to Heaven'. The species is commonly known and referred to by the commercial designation "Spreading Jacob's Ladder".

BRIEF SUMMARY OF THE INVENTION

The new variety was discovered at a nursery in Framingham, Mass., as a naturally occurring seedling (whole plant) mutation of the species *Polemonium reptans*. The *Polemonium reptans* seedling named 'Stairway to Heaven' came up variegated from seed collected from typical *Polemonium reptans* var. *reptans* growing in the nursery and has remained stable through four successive years of evaluation. The new cultivar 'Stairway to Heaven' is quite distinct from typical plants of *Polemonium reptans* var. *reptans* known to me and was discovered primarily due to its unique white and light green foliar variegation. During the winter, small, predominantly pink leaves cluster at soil level at the tips of active rhizomes.

Asexual reproduction of the new cultivar by tissue culture (micropropagation of rhizome buds) and by division of the rhizome and roots in Eastford and Kingston Conn., has shown that the unique features of the new *Polemonium* are firmly fixed and retained through successive generations of asexual reproduction. In other words, the new cultivar reproduces true to type in successive generations of asexual reproduction.

The new cultivar 'Stairway to Heaven' is particularly characterized by its variegated foliage which to the best knowledge of the inventor, is unique for the species. The parental (seed and pollen) parents exhibited non-variegated leaves of a uniform medium green (Pantone 575U) that is typical for the species *Polemonium reptans* var. *reptans*. Plants of the species, including the new cultivar, thrive best in moist, fertile soil and full sun to light shade.

The habit of the plant is a clumping perenial with a mount of basal leaves and branching stems with small cauline leaves and flowers in branched panicles. The leaves of 'Stairway to Heaven' are once odd-pinnately copound, with from 5 to 17 leaflets per leaf, averaging 13–15 on a typical basal leaf and 3–7 on upper cauline leaves. A few of the smallest leaves subtending the flowers may be simple. The leaflets have no petiolule, so are therefore sessile to the rachis. The leaf base is rounded on a typical leaflet but some leaflets have more of an acute base. The margin is entire. The rachis and petiole is a combination of Pantone 575 U, 5767U and 461C arranged in bands along the rachis and petiole bleeding into a deep purple red (Pantone 234U) toward the base of the petiole especially in colder weather.

The main foliage color is medium green but there is on the upper and lower surfaces of each leaflet either a smooth or ragged marginal band of creamy white (Pantone 461C) that extends $1/8^{th}$ to ½ of the way to the midvein. The center of a typical leaflet's upper surface is medium green (Pantone 575U), and at the location where the white and green meet, there is an irregular band of pale gray-green produced from a blending of the others (mix of Pantone 5767U and 5797U). The relative amount and distribution of the three colors (white, gray-green, and medium green) varies from leaflet to leaflet and from leaf to leaf. In general, the immature leaves have more marginal white banding, while on older and dehiscing leaves, the white changes to a shade darker creamy white (Pantone 460C). Some leaflets are all white or white with a thin pocket of green or gray-green toward the center. The white areas of immature, expanding leaves taken on a light pink tone (Pantone 230U) if grown in bright light or cool weather (<70 degrees F.), but the pink fades as the leaf becomes fully expanded and/or the weather warms. The lower leaf surface is a combination of a marginal band of creamy white (Pantone 461C) and a central patch of gray green (mix of Pantone 5767U and 5797U).

'Stairway to Heaven' has five sepals having a color of medium green (Pantone 575 U) fused along the lower half into a bell shape. The base of the bell is rounded and is 2 mm wide. The upper half or each sepal lobe has an elliptical shape with an acute tip. The total sepal length is 5 mm. The width of each individual sepal lobe at the widest point is 2 mm. The width of the calyx at the widest point is 6 mm.

Flower color is identical with the parental species, violet blue on both the upper and lower surfaces of the petals (Pantone 263U). Flowers are campanulate, 2 cm long and 16 mm wide, with a slight sweet fragrance. The corolla consists of five petals fused along the lower half into a narrow bell (3 mm at the base). The upper (free) half of each petal is oval with a rounded tip. Petal length from the base of the corolla to its tip is 2 cm. Individual petal width at its widest point is 6 mm. The pedicle length is 5–8 mm with a diameter of 1 mm and the coloration is medium green (Pantone 575U). Each flower has five stamens each about 2 cm from base to tip, and one e cm from base to tip, and one exerted pistil with 3 stigmatic lobes. The pistil is 24 cm long from base to tip. The ovary is superior and divided into three locules, each containing from 1–10 ovules. Fruits is an oval, tri-locular capsule with a rounded base and acute tip produced in, and partially enclosed by, the cup formed by the calyx. Mature fruit dimensions are 6–7 mm long and 4 mm wide at the widest point. The color of the fruit is medium green (Pantone 575U). Mature seeds are crescent shaped, 3 mm long and 1 mm wide in the middle, narrowing abruptly to an acute tip at both ends. Ripe seed is dark brown (Pantone 497C), rough in texture (under magnification), with a sunken pit (0.5 mm wide) on one side toward the center of the seed.

'Stairway to Heaven' has naked vegatative buds (no bud scales evident), the winter buds lie in groves along a creeping rhizome. The buds are 1–2 mm in diameter and length, ovoid in shape and develop deep red-purple coloration (Pantone 234U) during winter dormancy. During active growth, buds are obscured by the foliage.

In addition to the described comparison with typical plants of the species, including the parent cultivar, 'Stairway to Heaven' can be compared with the *Polemonium reptans* cultivar 'Album' (unpatented) which has white flowers and non-variegated foliage, and 'Blue Pearl' (unpatented) which is also non-variegated and has dark, blue-violet flowers. Additionally, 'Blue Pearl' has a very different habit than 'Stairway to Heaven'. The 'Blue Pearl' is taller (24–28 inches), and the stem and leaves are stiffer.

The cultivar 'Stairway to Heaven' has not been observed under all possible environmental conditions. The phenotype may vary somewhat with variations in environment such as temperature and light intensity without any variance in genotype. The following observations, measurements and comparisons describe a four year and three month old plant grown in Framingham, Mass. under conditions which closely approximate those generally used in commercial practice. 'Stairway to Heaven' has not been found to suffer from any particular disease or insect pest under cultivation in Framingham, Mass.

The following traits have been repeatedly observed and are determined to be the distinctive and unique characteristics of 'Stairway to Heaven'. These characteristics in combination distinguish 'Stairway to Heaven' as a new and distinct cultivae.

BRIEF DESCRIPTION OF THE DRAWING

The accompanying colored photographs illustrate the overall appearance of the new cultivar, showing the colors as true as it is reasonably possible to obtain in color reproductions of this type.

DETAILED BOTANICAL DESCRIPTION

The following is a detailed description of 'Stairway to Heaven' based on plants grown in Framingham, Mass. All color determinations and comparisons are based on The Pantone Color Formula Guide 747XR ($5^{th}$ Printing 1988–1989.

Classification:

*Origin.*—Naturally occurring seedling mutation discovered in a nursery in Framingham, Mass., USA.

*Parentage.*—Seedling from *Polemonium reptans.*

Plant:

*Habit.*—Clump forming, rhizomatous perennial.

*Size.*—Mature plants are 12–16 inches in height in bloom and 5–10 inches out of bloom with a spread of 14–18 inches.

*Root system.*—Moderately fleshy and fibrous roots originating from a creeping rhizome.

*Plant vigor.*—A perennial with excellent vigor. A flush of leaves and flowers appear as temperatures warm in spring, and with adequate moisture and fertility, new foliage will continue to be produced after flowering up until frost.

*Blooming habit.*—Plant sends up numerous branching stems from the rhizomes as weather warms in spring, each branchlet terminating in a cluster of from 1 to 15, half inch flowers.

*Blooming period.*—Total period of 14–21 days in mid-Spring. Depending on the weather, blooming can start as early as May $10^{th}$ or as late as June $5^{th}$.

*Method of asexual propagation.*—Preferably by tissue culture propagation, although asexual reproduction through division of the rhizomes is possible.

*Hardiness.*—USDA hardiness zones 3–9.

Foliage:

*Type.*—Compound, with 5 to 17 leaflets per leaf, averaging 13–15 leaflets on basal leaves and 5–9 leaflets on the cauline leaves. Some leaflets subtending branches of the inflorescence may have only 3 leaflets or be simple.

*Texture.*—Medium.

*Shape.*—Generally rounded. Leaves are narrowly pinnate; leaflets are elliptical.

*Length.*—Leaves are 3 to 7 inches long; leaflets are 1 to 2 inches long.

*Width.*—Leaves are 2 to 3¾ inches wide; leaflets are ½ to ¾ inches wide.

*Petiole length.*—5 to 6 inches (basal), 0 to 1½ inches (cauline).

*Margins.*—Entire.

*Apex* (*of leaflet*).—Acute.

*Base* (*of leaflet*).—Rounded, sessile to rachis.

Flowers:

*Form.*—Panicle.

*Borne.*—In terminal and auxiliary clusters of 3–5 from the tops of flowering stems on 1 to 3 inch branchlets. Each main flowering stem can produce 20 to 30 flowers.

*Petal count.*—Five of equal size. Each is ¼ inches long.

*Petal shape.*—Rounded and lobed nearly to the middle, lobes entire.

*Flower type.*—Campanulate.

*Flower size.*—Petals are ¼ inch long; flowers are ½ inch in diameter, pedicel ¼ to $\frac{3}{8}^{th}$ inch long, slender.

*Carpels.*—One carpel, which is longer than the stamens and slightly longer than the corolla.

*Stamen number.*—5. Each stamen is about as long as its corresponding petal.

Color characteristics:

*Foliage.*—Immature leaves, especially those developing in temperatures under 70° F. have a temporary pink coloration (Pantone 236 C) that suffuses those areas that will later turn white. Mature leaves are irregularly variegated with a margin of white (no Pantone equivalent, but it is a creamy or eggshell white), a center of dark green (Pantone 5615C) and at the location where the white and dark green meet, there is a band of gray green (Pantone 5773 C). Older leaves eventually replace some of the white color with a pale yellow-green (Pantone 585 C).

*Flowers.*—The color of the flowers most closely approximates Pantone 270 C, though exact color varies with air temperature and sun exposure at time of anthesis.

*Pistil.*—One pistil that is slightly exerted with a terminal style and 3 stigmas. The ovary is superior, triocular and contains 1–10 seeds per locule.

*Fragrance.*—Slight sweet fragrance.

Sepals:

*Number.*—5.

*Color.*—Medium green (Pantone 575U).

*Shape.*—Five sepals fused along lower half into a bell shape. Upper half is elliptical with an acute tip.

*Size.*—Base of bell is rounded and is 2 mm wide. Total sepal length is 5 mm. The width of each lobe the widest point is 2 mm. Width of the calyx is 6 mm.

Seed:

*Shape.*—Crescent shaped with a sunken pit on one side of 0.5 mm on one side toward the center of the seed.

*Size.*—3 mm long and 1 mm wide narrowing abruptly to a point at both ends.

*Color.*—Ripe seed is dark brown (Pantone 497C).

*Texture.*—Rough (under magnification).

Fruit:

*Color.*—Medium green (Pantone 575U).

*Shape.*—Oval, tri-locular capsule with a rounded base and acute tip produced in and partially enclosed by the cup formed by the calyx.

*Size.*—6–7 mm long and 4 mm wide at widest point.

Disease: None observed on plant grown in nursery in Framingham, Mass.

It is claimed:

1. A new and distinct variety of *Polemonium* plant named 'Stairway to Heaven', substantially as illustrated and described.

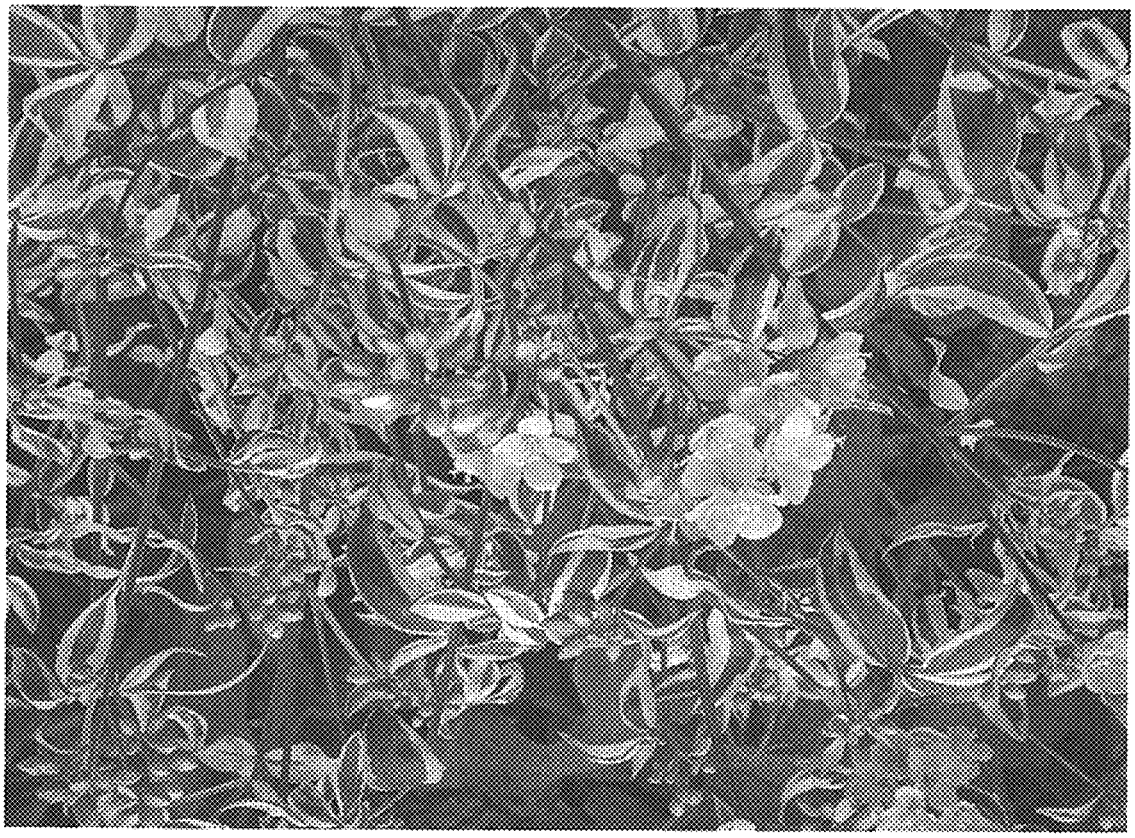

* * * * *